US006455574B1

(12) United States Patent
Buch

(10) Patent No.: US 6,455,574 B1
(45) Date of Patent: Sep. 24, 2002

(54) THERAPEUTIC COMBINATION

(75) Inventor: Jan Buch, Greenwich, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/512,914

(22) Filed: Feb. 25, 2000

Related U.S. Application Data

(63) Continuation of application No. PCT/IB98/01225, filed on Aug. 11, 1998.
(60) Provisional application No. 60/057,275, filed on Aug. 29, 1997.

(51) Int. Cl.$^7$ ...................... A61K 31/40; A61K 31/435; A61K 31/44
(52) U.S. Cl. ........................ 514/427; 514/277; 514/408; 514/422; 514/423; 514/356
(58) Field of Search ................................ 514/422, 423, 514/356, 427, 408, 277

(56) References Cited

U.S. PATENT DOCUMENTS

| | | | |
|---|---|---|---|
| 3,983,140 A | 9/1976 | Endo et al. | |
| 4,231,938 A | 11/1980 | Monaghan et al. | |
| 4,346,227 A | 8/1982 | Terghara et al. | |
| 4,444,784 A | 4/1984 | Hoffman et al. | |
| 4,448,784 A | 5/1984 | Glamkowski et al. | |
| 4,450,171 A | 5/1984 | Hoffman et al. | |
| 4,572,909 A | 2/1986 | Campbell et al. | 514/356 |
| 4,681,893 A | 7/1987 | Roth | 514/422 |
| 4,739,073 A | 4/1988 | Kathawala | |
| 4,804,770 A | 2/1989 | Karanewsky | |
| 4,879,303 A | 11/1989 | Davison et al. | |
| 4,920,123 A | 4/1990 | Beyer et al. | |
| 4,925,672 A | 5/1990 | Gremm et al. | |
| 5,155,120 A | 10/1992 | Lazar et al. | 514/356 |
| 5,273,995 A | 12/1993 | Roth | 514/422 |
| 5,385,929 A | 1/1995 | Bjorge et al. | |
| 5,447,922 A | 9/1995 | Lawrence et al. | |
| 5,502,199 A | 3/1996 | Angerbauer et al. | |
| 5,543,542 A | 8/1996 | Lawrence et al. | |
| 5,616,593 A | 4/1997 | Patel et al. | |
| 5,622,985 A | 4/1997 | Olukotun et al. | |
| 5,733,558 A | 3/1998 | Breton et al. | |

FOREIGN PATENT DOCUMENTS

| | | |
|---|---|---|
| DE | 19539363 A | 4/1997 |
| EP | 0363934 | 12/1993 |
| EP | 0709098 | 5/1996 |
| EP | 0738510 | 10/1996 |
| EP | 0753298 | 1/1997 |
| WO | WO 97/15291 | 5/1997 |
| WO | WO 9716184 | 5/1997 |

OTHER PUBLICATIONS

Messerli, Am. J. Hypertens. 1996, 9(12, pt. 2), 177S–181S.
Nawrocki et al., Arteriosclerosis, Thrombosis, and Vascular Biology, May 15, 1995, (5) 678–82.
Brown and Goldstein, New England Journal of Medicine, 1981, 305, No. 9, 515–517.
The Scandinavian Simvastatin Survival Study (4S), Lancet, 1994, 344, 1383–89.
Shepherd, J. et al., Prevention of coronary heart disease with pravastatin in men with hypercholesterolemia, New England Journal of Medicine, 1995, 333, 1301–07.
Wilson, et al., Am. J. Cardiol. 1987, 59(14): 91G–94G.
Kramsch et al., Journal of Human Hypertension (1995) Suppl. 1, S3–S9.
Lichtlen, P.R. et al., Retardation of angiographic progression of coronary artery disease by nifedipine, Lancet, 1990, 335, 1109–13.
Waters, D. et al., A controlled clinical trial to assess the effect of a calcium channel blocker on the progression of coronary atherosclerosis, Circulation, 1990, 82, 1940–53.
Orekhov et al., Cardiovascular Drugs and Therapy, 1997, 11, 350.
Jukema et al., Circulation, 1995, Suppl. 1, 1–197.
Jukema et al., Arteriosclerosis, Thrombosis, and Vascular Biology, vol. 16, No. 3, 1996, 425–430.
Orekhov A.N., et al., (1997) "Anthiatherosclerotic and Antitherogenic Effects of a Calcium Antagonist plus Statin Combination: Amlodipine and Lovastatin," Int. J. Cardiol., 62, Suppl. 2: S67–77.
Merck Index, $12^{th}$ Merck & Co., NJ, 1996, pp. 86–87, 714–715, 954–955, 1323 and 1465.
Davis and Cutler, et al., Am. Jrnl. of Hypertension, vol. 9, No. 4, Part 1, 1996, pp. 342–360.
Shen, et al., Low Dose Amlodipine Besylate und Perindopril Combined Therapy of Severe Aged Hypertension, CAPLUS, AN 1997: 13566, 1996.
Merck Index, $12^{th}$ Ed., 1996, pp. Ther. 1–3, 5, 10 and 11.
Ganotakis, E.S., et al., J. Drug Dev. Clin. Practice vol. 8, No. 2, Sep. 1996, pp. 57–60.
Biorganic & Medicinal Chemistry Letters, 1995 vol. 5. No. 5 pp. 427–430.
Bioorganic & Medicinal Chemistry Letter, 1996 vol. 6 No. 3 pp. 273–278.
XIIth International Symposium on Atherosclerosis, Stockholm, Sweden, Jun. 25–29, 2000.

(List continued on next page.)

*Primary Examiner*—Minna Moezie
*Assistant Examiner*—S. Jiang
(74) *Attorney, Agent, or Firm*—Peter C. Richardson; Gregg C. Benson; Robert T. Ronau

(57) ABSTRACT

This invention relates to pharmaceutical combinations of amlodipine or a pharmaceutically acceptable acid addition salt thereof and atorvastatin or a pharmaceutically acceptable salt thereof, kits containing such combinations and methods of using such combinations to treat subjects suffering from angina pectoris, atherosclerosis, combined hypertension and hyperlipidemia and to treat subjects presenting with symptoms of cardiac risk, including humans. This invention also relates to additive and synergistic combinations of amlodipine and atorvastatin whereby those synergistic combinations are useful in treating subjects suffering from angina pectoris, atherosclerosis, combined hypertension and hyperlipidemia and those subjects presenting with symptoms of cardiac risk, including humans.

12 Claims, No Drawings

OTHER PUBLICATIONS

Supplement to Journal of the American College or Cardiology, (Supplement A) vol. 37 No. 2, Feb. 2001, p. 253A.

Blood Pressure Control for the Hypertensive Patient, 1997 American Journal of Hypertension, vol. 14 (Suppl .2).

Ascot, The Anglo–Scandinavian Cardiac Outcomes Trail (Slide Presentation), May, 1997.

New Approaches to Atherosclerosis: An Overview; Peter McCarthy; Medical Research Reviews, vol.13, No. 2, 139–159 (1993).

British Hypertension Society Protocol; Dec. 3, 1993.

Noninvasive Tracking of Coronary Atherosclerosis by Electron Beam Computed Tomography; Rationale and Design of the Felodipine Atherosclerosis Prevention Study (FAPS); Nathan D. Wong PhD; et al; Am. J. Of Cardiology; vol. 76, 1239–1242 (1995).

Rationale and Design for the Antihypertensive and Lipid Lowering Treatment to Prevent Heart Attack Trial (ALLHAT); Barry R. Davis, et al; AJH vol. 9, No. 4, 342–360 (1995).

DJB Publications Ltd. 1997, Scrip. No. 2235/36 May 27/30th 1997.

Anglo–Scandinavian ASCOT Cardiac Outcomes Trial Press Kit., May 1997.

The hypertension trials, Peter S. Sever and Judith A. MacKay, Journal of Hypertension 1996, vol. 14 (Supp. 2) S29–S34.

Blood Pressure Control for the Hypertensive Patent, What Can We Do Better?, Peter S. Sever, AJH 1997; 10.128S–130S.

British Hypertension Society Letter dated Jul. 3, 1996.

Merck Index, 12th Merck & Co, NJ, 1996, pp. 86, 87, 714, 715, 954, 955, 1323, and 1465.

THERAPEUTIC COMBINATION

This application claims priority from copending International Patent Application Number PCT/IB98/01225 filed Aug. 11, 1998, which claims priority from U.S. Provisional Application No. 60/057,275, filed Aug. 29, 1997.

This invention relates to pharmaceutical combinations of amlodipine and pharmaceutically acceptable acid addition salts thereof and atorvastatin and pharmaceutically acceptable salts thereof, kits containing such combinations and methods of using such combinations to treat subjects suffering from angina pectoris, atherosclerosis, combined hypertension and hyperlipidemia and to treat subjects presenting with symptoms of cardiac risk, including humans. This invention also relates to additive and synergistic combinations of amlodipine and atorvastatin whereby those additive and synergistic combinations are useful in treating subjects suffering from angina pectoris, atherosclerosis, combined hypertension and hyperlipidemia and those subjects presenting with symptoms or signs of cardiac risk, including humans.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium, disclosed in U.S. Pat. No. 5,273,995, which is incorporated herein by reference, is currently sold as Lipitor° and has the formula

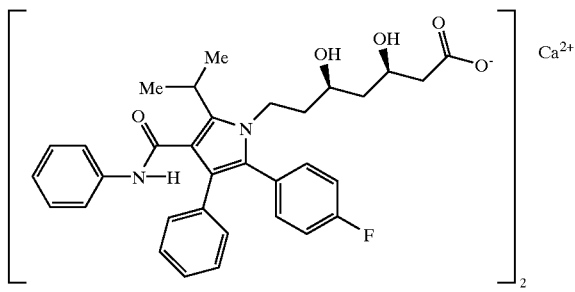

Atorvastatin calcium is a selective, competitive inhibitor of HMG-CoA. As such, atorvastatin calcium is apotent lipid lowering compound. The free carboxylic acid form of atorvastatin exists predominantly as the lactone of the formula

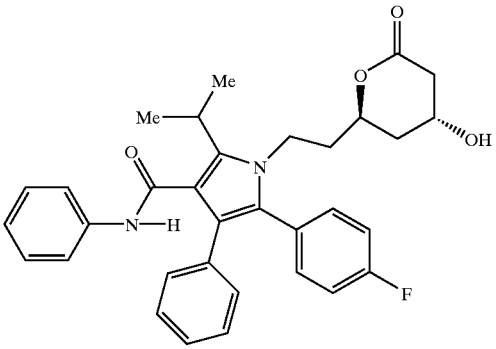

and is disclosed in U.S. Pat. No. 4,681,893, which is incorporated herein by reference.

Amlodipine and related dihydropyridine compounds are disclosed in U.S. Pat. No. 4,572,909, which is incorporated herein by reference, as potent ant-ischemic and antihypertensive agents. U.S. Pat. No. 4,879,303, which is incorporated herein by reference, discloses amlodipine benzenesulfonate salt (also termed amlodipine besylate). Amlodipine and amlodipine besylate are potent and long lasting calcium channel blockers. As such, amlodipine, amlodipine besylate and other pharmaceutically acceptable acid addition salts of amlodipine have utility as antihypertensive agents and as antiischemic agents. Amlodipine and its pharmaceutically acceptable acid addition salts are also disclosed in U.S. Pat. No. 5,155,120 as having utility in the treatment of congestive heart failure. Amlodipine besylate is currently sold as Norvasc®. Amlodipine has the formula

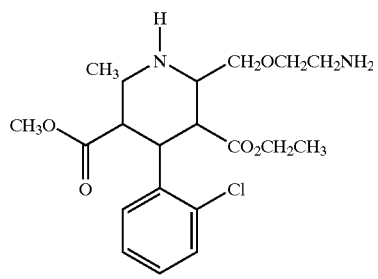

Atherosclerosis is a condition characterized by irregularly distributed lipid deposits in the intima of arteries, including coronary, carotid and peripheral arteries. Atherosclerotic coronary heart disease (hereinafter termed "CHD") accounts for 53% of all deaths attributable to a cardiovascular event. CHD accounts for nearly one-half (about $50–60 billion) of the total U.S. cardiovascular healthcare expenditures and about 6% of the overall national medical bill each year. Despite attempts to modify secondary risk factors such as, inter alia, smoking, obesity and lack of exercise, and treatment of dyslipidemia with dietary modification and drug therapy, CHD remains the most common cause of death in the United States.

High levels of blood cholesterol and blood lipids are conditions involved in the onset of atherosclerosis. It is well known that inhibitors of 3-hydroxy-3-methylglutaryl-coenzyme A reductase (HMG-CoA reductase) are effective in lowering the level of blood plasma cholesterol, especially low density lipoprotein cholesterol (LDL-C), in man (Brown and Goldstein, New England Journal of Medicine, 1981, 305, No. 9, 515–517). It has now been established that lowering LDL-C levels affords protection from coronary heart disease (see, e.g., The Scandinavian Simvastatin Survival Study Group: Randomised trial of cholesterol lowering in 4444 patients with coronary heart disease: the Scandinavian Simvastatin Survival Study (4S), Lancet, 1994, 344, 1383–89; and Shepherd, J. et al., Prevention of coronary heart disease with pravastatin in men with hypercholesterolemia, New England Journal of Medicine, 1995, 333,1301–07).

Angina pectoris is a severe constricting pain in the chest, often radiating from the precordium to the left shoulder and down the left arm. Often angina pectoris is due to ischemia of the heart and is usually caused by coronary disease.

Currently the treatment of symptomatic angina pectoris varies significantly from country to country. In the U.S., patients who present with symptomatic, stable angina pectoris are frequently treated with surgical procedures or PTCA. Patients who undergo PTCA or other surgical procedures designed to treat angina pectoris frequently experience complications such as restenosis. This restenosis may be manifested either as a short term proliferative response to angioplasty-induced trauma or as long term progression of the atherosclerotic process in both graft vessels and angioplastied segments.

The symptomatic management of angina pectoris involves the use of a number of drugs, frequently as a combination of two or more of the following classes: beta blockers, nitrates and calcium channel blockers. Most, if not all, of these patients require therapy with a lipid lowering agent as well. The National Cholesterol Education Program (NCEP) recognizes patients with existing coronary artery disease as a special class requiring aggressive management of raised LDL-C.

Amlodipine helps to prevent myocardial ischemia in patients with exertional angina pectoris by reducing Total Peripheral Resistance, or afterload, which reduces the rate pressure product and thus myocardial oxygen demand at any particular level of exercise. In patients with vasospastic angina pectoris, amlodipine has been demonstrated to block constriction and thus restore myocardial oxygen supply. Further, amlodipine has been shown to increase myocardial oxygen supply by dilating the coronary arteries.

Hypertension frequently coexists with hyperlipidemia and both are considered to be major risk factors for developing cardiac disease ultimately resulting in adverse cardiac events. This clustering of risk factors is potentially due to a common mechanism. Further, patient compliance with the management of hypertension is generally better than patient compliance with hyperlipidemia. It would therefore be advantageous for patients to have a single therapy which treats both of these conditions.

Coronary heart disease is a multifactorial disease in which the incidence and severity are affected by the lipid profile, the presence of diabetes and the sex of the subject. Incidence is also affected by smoking and left ventricular hypertrophy which is secondary to hypertension. To meaningfully reduce the risk of coronary heart disease, it is important to manage the entire risk spectrum. For example, hypertension intervention trials have failed to demonstrate full normalization in cardiovascular mortality due to coronary heart disease. Treatment with cholesterol synthesis inhibitors in patients with and without coronary artery disease reduces the risk of cardiovascular morbidity and mortality.

The Framingham Heart Study, an ongoing prospective study of adult men and women, has shown that certain risk factors can be used to predict the development of coronary heart disease. (see Wilson et al., Am. J. Cardiol. 1987, 59(14):91G–94G). These factors include age, gender, total cholesterol level, high density lipoprotein (HDL) level, systolic blood pressure, cigarette smoking, glucose intolerance and cardiac enlargement (left ventricular hypertrophy on electrocardiogram, echocardiogram or enlarged heart on chest X-ray). Calculators and computers can easily be programmed using a multivariate logistic function that allows calculation of the conditional probability of cardiovascular events. These determinations, based on experience with 5,209 men and women participating in the Framingham study, estimate coronary artery disease risk over variable periods of follow-up. Modeled incidence rates range from less than 1% to greater than 80% over an arbitrarily selected six year interval. However, these rates are typically less than 10% and rarely exceed 45% in men and 25% in women.

Kramsch et al., Journal of Human Hypertension (1995) (Suppl. 1), 53–59 disclose the use of calcium channel blockers, including amlodipine, to treat atherosclerosis. That reference further suggests that atherosclerosis can be treated with a combination of amlodipine and a lipid lowering agent. Human trials have shown that calcium channel blockers have beneficial effects in the treatment of early atherosclerotic lesions. (see, e.g., Lichtlen, P. R. et al., Retardation of angiographic progression o coronary artery disease by nifedipine, Lancet, 1990, 335, 1109–13; and Waters, D. et al., A controlled clinical trial to assess the effect of a calcium channel blocker on the progression of coronary atherosclerosis, Circulation, 1990, 82, 1940–53.) U.S. Pat. No. 4,681,893 discloses that certain statins, including atorvastatin, are hypolipidemic agents and as such are useful in treating atherosclerosis. Jukema et al., Circulation, 1995 (Suppl. 1), 1–197, disclose that there is evidence that calcium channel blockers act synergistically in combination with lipid lowering agents (e.g., HMG-CoA reductase inhibitors), specifically pravastatin. Orekhov et al., Cardiovascular Drugs and Therapy, 1997, 11, 350 disclose the use of amlodipine in combination with lovastatin for the treatment of atherosclerosis.

SUMMARY OF THE INVENTION

This invention is directed to a pharmaceutical composition, hereinafter termed "Composition A", comprising:

a. an amount of amlodipine or a pharmaceutically acceptable acid addition salt thereof;

b. an amount of atorvastatin or a pharmaceutically acceptable salt thereof; and c. a pharmaceutically acceptable carrier or diluent.

This invention is particularly directed to a pharmaceutical composition, hereinafter termed "Composition AA", of Composition A comprising amlodipine besylate.

This invention is more particularly directed to a pharmaceutical composition, hereinafter termed "Composition AB", of Composition A comprising the hemicalcium salt of atorvastatin.

This invention is also directed to a first pharmaceutical composition, hereinafter termed "Composition B", for use with a second pharmaceutical composition for achieving a antihypertensive effect and a hypolipidemic effect in a mammal suffering from hypertension and hyperlipidemia, which effects are greater than the sum of the antihypertensive and hypolipidemic effects achieved by administering said first and second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition BA", of Composition B wherein said second pharmaceutical composition comprises amlodipine besylate.

This invention is more particularly directed to a first pharmaceutical composition, hereinafter termed "Composition BB", of Composition BA comprising the hemicalcium salt of atorvastatin.

This invention is also directed to a first pharmaceutical composition, hereinafter termed "Composition C", for use with a second pharmaceutical composition for achieving a antihypertensive effect and a hypolipidemic effect in a mammal suffering from hypertension and hyperlipidemia, which effects are greater than the sum of the antihypertensive and hypolipidemic effects achieved by administering said first and second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent.

This invention is particularly directed to a first pharmaceutical composition, hereinafter termed "Composition CA", of Composition C comprising amlodipine besylate.

This invention is more particularly directed to a first pharmaceutical composition, hereinafter termed "Composition CB", of Composition CA wherein said second pharmaceutical composition comprises the hemicalcium salt of atorvastatin.

This invention is also directed to a first pharmaceutical composition, hereinafter termed "Composition D", for use with a second pharmaceutical composition for achieving a antihypertensive effect and a hypolipidemic effect in a mammal suffering from hypertension and hyperlipidemia, which effects are greater than the antihypertensive and hypolipidemic effects achieved by administering said first or second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent.

This invention is particularly directed to a first pharmaceutical composition, hereinafter termed "Composition DA", of Composition D comprising amlodipine besylate.

This invention is more particularly directed to a first pharmaceutical composition, hereinafter termed "Composition DB", of Composition DA wherein said second pharmaceutical composition comprises the hemicalcium salt of atorvastatin.

This invention is also directed to a first pharmaceutical composition, hereinafter termed "Composition E", for use with a second pharmaceutical composition for achieving a antihypertensive effect and a hypolipidemic effect in a mammal suffering from hypertension and hyperlipidemia, which effects are greater than the antihypertensive and hypolipidemic effects achieved by administering said first or second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition EA", of Composition E wherein said second pharmaceutical composition comprises amlodipine besylate.

This invention is more particularly directed to a first pharmaceutical composition, hereinafter termed "Composition EB" of Composition EA comprising the hemicalcium salt of atorvastatin.

This invention is also directed to a first pharmaceutical composition, hereinafter termed "Composition F", for use with a second pharmaceutical composition for achieving an antianginal effect in a mammal suffering from angina pectoris, which effect is greater than the sum of the antiangina effects achieved by administering said first and second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent.

This invention is particularly directed to a first pharmaceutical composition, hereinafter termed "Composition FA", of Composition F comprising amlodipine besylate.

This invention is more particularly directed to a first pharmaceutical composition, hereinafter termed "Composition FB", of Composition FA wherein said second pharmaceutical composition comprises the hemicalcium salt of atorvastatin.

This invention is also directed to a first pharmaceutical composition, hereinafter termed "Composition G", for use with a second pharmaceutical composition for achieving an antianginal effect in a mammal suffering from angina pectoris, which effect is greater than the sum of the antiangina effects achieved by administering said first and second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition G", of Composition G wherein said second pharmaceutical composition comprises amlodipine besylate.

This invention is more particularly directed to a first pharmaceutical composition, hereinafter termed "Composition GB", of Composition G comprising the hemicalcium salt of atorvastatin.

This invention is also directed to a first pharmaceutical composition, hereinafter termed "Composition H", for use with a second pharmaceutical composition for achieving an antianginal effect in a mammal suffering from angina pectoris, which effect is greater than the antianginal effects achieved by administering said first or second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent. acceptable carrier or diluent.

This invention is particularly directed to a first pharmaceutical composition, hereinafter termed "Composition HA", of Composition H comprising amlodipine besylate.

This invention is more particularly directed to a first pharmaceutical composition, hereinafter termed "Composition HB", of Composition HA wherein said second pharmaceutical composition comprises the hemicalcium salt of atorvastatin.

This invention is also directed to a first pharmaceutical composition, hereinafter termed "Composition J", for use with a second pharmaceutical composition for achieving an antianginal effect in a mammal suffering from angina pectoris, which effect is greater than the antianginal effects achieved by administering said first or second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition JA", of Composition J wherein said second pharmaceutical composition comprises amlodipine besylate.

This invention is more particularly directed to a first pharmaceutical composition, hereinafter termed "Composition JB", of Composition JA comprising the hemicalcium salt of atorvastatin.

This invention is also directed to a first pharmaceutical composition, hereinafter termed "Composition K", for use with a second pharmaceutical composition for achieving an antiatherosclerotic effect in a mammal, which effect is greater than the sum of the antiatherosclerotc effects achieved by administering said first and second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition KA", of Composition K wherein said second pharmaceutical composition comprises amlodipine besylate.

This invention is more particularly directed to a first pharmaceutical composition, hereinafter termed "Composition KB", of Composition KA comprising the hemicalcium salt of atorvastatin.

This invention is still more particularly directed to a composition, hereinafter termed "Composition KC", of Composition KB wherein said antiatherosclerotic effect is manifested by a slowing of the progression of atherosclerotic plaques.

This invention is still more particularly directed to a composition of Composition KC wherein said progression of atherosclerotic plaques is slowed in coronary arteries.

This invention is also particularly directed to a composition of Composition KB wherein said progression of atherosclerotic plaques is slowed in carotid arteries.

This invention is also particularly directed to a composition of Composition KB wherein said progression of atherosclerotic plaques is slowed in the peripheral arterial system.

This invention is more particularly directed to a composition, hereinafter termed "Composition KD", of Composition KB wherein said antiatherosclerotic effect is manifested by a regression of atherosclerotic plaques.

This invention is still more particularly directed to a composition of Composition KD wherein said regression of atherosclerotic plaques occurs in coronary arteries.

This invention is also particularly directed to a composition of Composition KD wherein said regression of atherosclerotic plaques occurs in carotid arteries.

This invention is also particularly directed to a composition of Composition KD wherein said regression of atherosclerotic plaques occurs in the peripheral arterial system.

This invention is also directed to a first pharmaceutical composition, hereinafter termed "Composition L", for use with a second pharmaceutical composition for achieving an antiatherosclerotic effect in a mammal, which effect is greater than the sum of the antiatherosclerotic effects achieved by administering said first and second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent.

This invention is particularly directed to a first pharmaceutical composition, hereinafter termed "Composition LA", of Composition L comprising amlodipine besylate.

This invention is more particularly directed to a first pharmaceutical composition, hereinafter termed "Composition LB", of Composition LA wherein said second pharmaceutical composition comprises the hemicalcium salt of atorvastatin.

This invention is still more particularly directed to a composition, hereinafter termed "LC", of Composition LB wherein said antiatherosclerotic effect is manifested by a slowing of the progression of atherosclerotic plaques.

This invention is still more particularly directed to a composition of Composition LC wherein said progression of atherosclerotic plaques is slowed in coronary arteries.

This invention is also particularly directed to a composition of Composition LC wherein said progression of atherosclerotic plaques is slowed in carotid arteries.

This invention is also particularly directed to a composition of Composition LC wherein said progression of atherosclerotic plaques is slowed in the peripheral arterial system.

This invention is more particularly directed to a composition, hereinafter termed "Composition LD", of Composition LB wherein said antiatherosclerotic effect is manifested by a regression of atherosclerotic plaques.

This invention is still more particularly directed to a composition of Composition LD wherein said regression of atherosclerotic plaques occurs in coronary arteries.

This invention is also particularly directed to a composition of Composition LD wherein said regression of atherosclerotic plaques occurs in carotid arteries.

This invention is also particularly directed to a composition of Composition LD wherein said regression of atherosclerotic plaques occurs in the peripheral arterial system.

This invention is also directed to a first pharmaceutical composition, hereinafter termed "Composition M", for use with a second pharmaceutical composition for achieving an antiatherosclerotic effect in a mammal, which effect is greater than the antiatherosclerotic effects achieved by administering said first or second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent.

This invention is particularly directed to a first pharmaceutical composition, hereinafter termed "Composition MA", of Composition M comprising amlodipine besylate.

This invention is more particularly directed to a first pharmaceutical composition, hereinafter termed "Composition MB", of Composition MA wherein said second pharmaceutical composition comprises the hemicalcium salt of atorvastatin.

This invention is still more particularly directed to a composition, hereinafter termed "Composition MC", of Composition MB wherein said antiatherosclerotic effect is manifested by a slowing of the progression of atherosclerotic plaques.

This invention is still more particularly directed to a composition of Composition MC wherein said progression of atherosclerotic plaques is slowed in coronary arteries.

This invention is also particularly directed to a composition of Composition MC wherein said progression of atherosclerotic plaques is slowed in carotid arteries.

This invention is also particularly directed to a composition of Composition MC wherein said progression of atherosclerotic plaques is slowed in the peripheral arterial system.

This invention is more particularly directed to a composition, hereinafter termed "Composition MD", of Composition MB wherein said antiatherosclerotic effect is manifested by a regression of atherosclerotic plaques.

This invention is still more particularly directed to a composition of Composition MD wherein said regression of atherosclerotic plaques occurs in coronary arteries.

This invention is also particularly directed to a composition of Composition MD wherein said regression of atherosclerotic plaques occurs in carotid arteries.

This invention is also particularly directed to a composition of Composition MD wherein said regression of atherosclerotic plaques occurs in the peripheral arterial system.

This invention is also directed to a first pharmaceutical composition, hereinafter termed "Composition N", for use with a second pharmaceutical composition for achieving an antiatherosclerotic effect in a mammal, which effect is greater than the antiatherosclerotic effects achieved by administering said first or second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition NA", of Composition N wherein said second pharmaceutical composition comprises amlodipine besylate.

This invention is more particularly directed to a first pharmaceutical composition, hereinafter termed "Composition NB", of Composition NA comprising the hemicalcium salt of atorvastatin.

This invention is still more particularly directed to a composition, hereinafter termed "Composition NC", of Composition NB wherein said antiatherosclerotic effect is manifested by a slowing of the progression of atherosclerotic plaques.

This invention is still more particularly directed to a composition of Composition NC wherein said progression of atherosclerotic plaques is slowed in coronary arteries.

This invention is also particularly directed to a composition of Composition NC wherein said progression of atherosclerotic plaques is slowed in carotid arteries.

This invention is also particularly directed to a composition of Composition NC wherein said progression of atherosclerotic plaques is slowed in the peripheral arterial system.

This invention is more particularly directed to a composition, hereinafter termed "Composition ND", of Composition NB wherein said antiatherosclerotic effect is manifested by a regression of atherosclerotic plaques.

This invention is still more particularly directed to a composition of Composition ND wherein said regression of atherosclerotic plaques occurs in coronary arteries.

This invention is also particularly directed to a composition of Composition ND wherein said regression of atherosclerotic plaques occurs in carotid arteries.

This invention is also particularly directed to a composition of Composition ND wherein said regression of atherosclerotic plaques occurs in the peripheral arterial system.

This invention is also directed to a first pharmaceutical composition, hereinafter termed "Composition P", for use with a second pharmaceutical composition for managing cardiac risk in a mammal at risk of suffering an adverse cardiac event, which effect is greater than the sum of the cardiac risk management effects achieved by administering said first and second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable add addition salt thereof and a pharmaceutically acceptable carrier or diluent.

This invention is particularly directed to a first pharmaceutical composition, hereinafter termed "Composition PA", of Composition P comprising amlodipine besylate.

This invention is more particularly directed to a first pharmaceutical composition of Composition PA wherein said second pharmaceutical composition comprises the hemicalcium salt of atorvastatin.

This invention is also directed to a first pharmaceutical composition, hereinafter termed "Composition Q", for use with a second pharmaceutical composition for managing cardiac risk in a mammal at risk of suffering an adverse cardiac event, which effect is greater than the sum of the cardiac risk management effects achieved by administering said first and second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition QA", of Composition Q wherein said second pharmaceutical composition comprises amlodipine besylate.

This invention is more particularly directed to a first pharmaceutical composition of Composition QA comprising the hemicalcium salt of atorvastatin.

This invention is also directed to a first pharmaceutical composition, hereinafter termed "Composition R", for use with a second pharmaceutical composition for managing cardiac risk in a mammal at risk of suffering an adverse cardiac event, which effect is greater than the cardiac risk management effects achieved by administering said first or second pharmaceutical compositions separately and which second pharmaceutical composition comprises an amount of atorvastatin or a pharmaceutically acceptable salt thereof and a pharmaceutically acceptable carrier or diluent, said first pharmaceutical composition comprising an amount of amlodipine or a pharmaceutically acceptable acid addition salt thereof and a pharmaceutically acceptable carrier or diluent.

This invention is particularly directed to a first pharmaceutical composition, hereinafter termed "Composition RAD", of Composition R comprising amlodipine besylate.

This invention is more particularly directed to a first pharmaceutical composition of Composition RA wherein said second pharmaceutical composition comprises the hemicalcium salt of atorvastatin.

This invention is also directed to a first pharmaceutical composition, hereinafter termed "Composition S", for use with a second pharmaceutical composition for managing cardiac risk in a mammal at risk of suffering an adverse cardiac event, which effect is greater than the cardiac risk management effects achieved by administering said first or second pharmaceutical compositions separately and which second pharmaceutical composition comprises an amount of amlodipine or a pharmaceutically acceptable acid addition salt thereof and a pharmaceutically acceptable carrier or diluent, said first pharmaceutical composition comprising an amount of atorvastatin or a pharmaceutically acceptable salt thereof and a pharmaceutically acceptable carrier or diluent.

This invention is particularly directed to a first pharmaceutical composition, hereinafter termed "Composition SA", of Composition S wherein said second pharmaceutical composition comprises amlodipine besylate.

This invention is more particularly directed to a first pharmaceutical composition of Composition S comprising the hemicalcium salt of atorvastatin.

This invention is also directed to a kit, hereinafter termed "Kit A", for achieving a therapeutic effect in a mammal comprising:
 a. an amount of amlodipine or a pharmaceutically acceptable acid addition salt thereof and a pharmaceutically acceptable carrier or diluent in a first unit dosage form;
 b. an amount of atorvastatin or a pharmaceutically acceptable salt thereof and a pharmaceutically acceptable carrier or diluent in a second unit dosage form; and
 c. container means for containing said first and second dosage forms.

This invention is particularly directed to a kit, hereinafter termed "Kit M", of Kit A comprising amlodipine besylate.

This invention is more particularly directed to a kit, hereinafter termed "Kit AB", of Kit AA comprising the hemicalcium salt of atorvastatin.

This invention is still more particularly directed to a kit, hereinafter termed "Kit AC", of Kit AB wherein said therapeutic effect is treatment of hypertension and hyperlipidemia.

This invention is still more particularly directed to a kit, hereinafter termed "Kit AD", of Kit AB wherein said therapeutic effect is treatment of angina pectoris.

This invention is also particularly directed to a kit, hereinafter termed "Kit AE" of Kit AB wherein said therapeutic effect is management of cardiac risk.

This invention is also particularly directed to a kit, hereinafter termed "Kit AF", of Kit AB wherein said therapeutic effect is treatment of atherosclerosis.

This invention is still more particularly directed to a kit, hereinafter termed "Kit AG", of Kit AF wherein said treatment of atherosclerosis slows the progression of atherosclerotic plaques.

This invention is further directed to a kit, hereinafter termed "Kit AH", of Kit AG wherein said progression of atherosclerotic plaques is slowed in coronary arteries.

This invention is still further directed to a kit, hereinafter termed "Kit AJ", of Kit AG wherein said progression of atherosclerotic plaques is slowed in carotid arteries.

This invention is still further directed to a kit, hereinafter termed "Kit AK", of Kit AG wherein said progression of atherosclerotic plaques is slowed in the peripheral arterial system.

This invention is still further directed to a kit, hereinafter termed "Kit AL", of Kit AF wherein said treatment of atherosclerosis causes the regression of atherosclerotic plaques.

This invention is still further directed to a kit of Kit AL wherein said regression of atherosclerotic plaques occurs in coronary arteries.

This invention is still further directed to a kit of Kit AL wherein said regression of atherosclerotic plaques occurs in carotid arteries.

This invention is still further directed to a kit of Kit AL wherein said regression of atherosclerotic plaques occurs in the peripheral arterial system.

This invention is also directed to a method, hereinafter termed "Method A", for treating a mammal in need of therapeutic treatment comprising administering to said mammal
 (a) an amount of a first compound, said first compound being amlodipine or a pharmaceutically acceptable acid addition salt thereof; and
 (b) an amount of a second compound, said second compound being atorvastatin or a pharmaceutically acceptable salt thereof;
wherein said first compound and said second compound are each optionally and independently administered together with a pharmaceutically acceptable carrier or diluent.

This invention is particularly directed to a method, hereinafter Method B, of Method A comprising amlodipine besylate.

This invention is more particularly directed to a method, hereinafter termed "Method C", of Method B comprising the hemicalcium salt of atorvastatin.

This invention is still more particularly directed to a method, hereinafter termed "Method D", of Method A wherein said first compound and said second compound are administered simultaneously.

This invention is still more particularly directed to a method, hereinafter termed "Method E", of Method A wherein said first compound and said second compound are administered sequentially in either order.

This invention is also particularly directed to a method, hereinafter termed "Method F", of Method C wherein said first compound and said second compound are administered simultaneously.

This invention is further directed to a method, hereinafter termed "Method G", of Method C wherein said first compound and said second compound are administered sequentially in either order.

This invention is still further directed to a method of Method A wherein said therapeutic treatment comprises antihypertensive treatment and antihyperlipidemic treatment.

This invention is still further directed to a method of Method F wherein said therapeutic treatment comprises antihypertensive treatment and antihyperlipidemic treatment.

This invention is still further directed to a method of Method G wherein said therapeutic treatment comprises antihypertensive treatment and antihyperlipidemic treatment.

This invention is further directed to a method of Method A wherein said therapeutic treatment comprises antianginal treatment.

This invention is further directed to a method of Method F wherein said therapeutic treatment comprises antianginal treatment.

This invention is further directed to a method of Method G wherein said therapeutic treatment comprises antianginal treatment.

This invention is further directed to a method of Method A wherein said therapeutic treatment comprises cardiac risk management.

This invention is further directed to a method of Method F wherein said therapeutic treatment comprises cardiac risk management.

This invention is further directed to a method of Method G wherein said therapeutic treatment comprises cardiac risk management.

This invention is further directed to a method of Method A wherein said therapeutic treatment comprises antiatherosclerotic treatment.

This invention is further directed to a method of Method F wherein said therapeutic treatment comprises antiatherosclerotic treatment.

This invention is further directed to a method of Method G wherein said therapeutic treatment comprises antiatherosclerotic treatment.

Amlodipine is a racemic compound due to the symmetry at position 4 of the dihydropyridine ring. The R and S enantiomers may be prepared as described by Arrowsmith et al., J. Med. Chem., 1986, 29, 1696. The calcium channel blocking activity of amlodipine is substantially confined to the S(−) isomer and to the racemic mixture containing the R(+) and S(−) forms. (see International Patent Application Number PCT/EP94/02697). The R(+) isomer has little or no calcium channel blocking activity. However, the R(+) isomer is a potent inhibitor of smooth muscle cell migration. Thus, the R(+) isomer is useful in the treatment or prevention of atherosclerosis. (see International Patent Application Number PCT/EP95/00847). Based on the above, a skilled person could choose the R(+) isomer, the S(−) isomer or the racemic mixture of the R(+) isomer and the S(−) isomer for use in the combination of this invention.

Where used herein, the term "cardiac risk", means the likelihood that a subject will suffer a future adverse cardiac event such as, e.g., myocardial infarction, cardiac arrest, cardiac failure, cardiac ischaemia. Cardiac risk is calculated using the Framingham Risk Equation as set forth above. The term "cardiac risk management" means that the risk of future adverse cardiac events is substantially reduced.

DETAILED DESCRIPTION OF THE INVENTION

The pharmaceutical compositions of this invention comprise amlodipine or a pharmaceutically acceptable acid addition salt thereof and/or atorvastatin or a pharmaceutically acceptable salt thereof.

Amlodipine may readily be prepared as described in U.S. Pat. No. 4,572,909 which is incorporated herein by reference. Amlodipine besylate, which is currently sold as Norvasc®, may be prepared as described in U.S. Pat. No. 4,879,303, which is incorporated herein by reference. Amlodipine and amlodipine besylate are potent and long lasting calcium channel blockers.

The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, besylate, succinate, citrate, methanesulfonate (mesylate) and p-toluenesulfonate (tosylate) salts.

Other acid addition salts of amlodipine may be prepared by reacting the free base form of amlodipine with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base of amlodipine and the acid are usually combined in a co-solvent from which the desired salt precipitates, or can be otherwise isolated by concentration and/or addition of a non-solvent.

Atorvastatin may readily be prepared as described in U.S. Pat. No. 4,681,892, which is incorporated herein by reference. The hemicalcium salt of atorvastatin, which is currently sold as Lipitor®, may readily be prepared as described in U.S. Pat. No. 5,273,995, which is incorporated herein by reference.

The expression "pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Other pharmaceutically-acceptable cationic salts of atorvastatin may be readily prepared by reacting the free add form of atorvastatin with an appropriate base, usually one equivalent in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent In many cases, salts are preferably prepared by mixing a solution of the acid with a solution of a different salt of the cation (e.g., sodium or potassium ethylhexanoate, magnesium oleate) and employing a solvent (e.g., ethyl acetate) from which the desired cationic salt precipitates. The salts may also be isolated by concentrating the reaction solution and/or by adding a non-solvent.

The acid addition salts of atorvastatin may be readily prepared by reacting the free base form of atorvastatin with the appropriate add. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent In addition, amlodipine, pharmaceutically acceptable acid addition salts thereof, atorvastatin and pharmaceutically acceptable salts thereof may occur as hydrates or solvates. Said hydrates and solvates are also within the scope of the invention.

The pharmaceutical combinations and methods of this invention are all adapted to therapeutic use as agents in the treatment of atherosclerosis, angina pectoris, and a condition characterized by the presence of both hypertension and hyperlipidemia in mammals, particularly humans. Further, since these diseases and conditions are closely related to the development of cardiac disease and adverse cardiac conditions, these combinations and methods, by virtue of their action as antiatherosclerotic, antianginals, antihypertensives and antihyperlipidemics, are useful in the management of cardiac risk.

The utility of the compounds of the present invention as medical agents in the treatment of atherosclerosis in mammals (e.g. humans) is demonstrated by the activity of the compounds of this invention in conventional assays and the clinical protocol described below:

Effect of Amlodipine and Atorvastatin, Alone and in Combination, on the Treatment of Atherosclerosis This study is a prospective randomized evaluation of the effect of a combination of amlodipine and atorvastatin on the progression/regression of coronary and carotid artery disease. The study is used to show that a combination of amlodipine and atorvastatin is effective in sowing or arresting the progression or causing regression of existing coronary artery disease (CAD) as evidenced by changes in coronary angiography or carotid ultrasound, in subjects with established disease.

This study is an angiographic documentation of coronary artery disease carried out as a double-blind, placebo-controlled trial of a minimum of about 500 subjects and preferably of about 780 to about 1200 subjects. It is especially preferred to study about 1200 subjects in this study. Subjects are admitted into the study after satisfying certain entry criteria set forth below.

Entry criteria: Subjects accepted for entry into this trial must satisfy certain criteria. Thus the subject must be an adult, either male or female, aged 18–80 years of age in whom coronary angiography is clinically indicated. Subjects will have angiographic presence of a significant focal lesion such as 30% to 50% on subsequent evaluation by quantitative coronary angiography (QCA) in a minimum of one segment (non-PTCA, non-bypassed or non-MI vessel that is judged not likely to require intervention over the next 3 years. It is required that thee segments undergoing analysis have not been interfered with. Since percutaneous transluminal cardiac angioplasty (PTCA) interferes with segments by the insertion of a balloon catheter, non-PTCA segments are required for analysis. It is also required that the segments to be analyzed have not suffered a thrombotic event, such as a myocardial infarct (MI). Thus the requirement for non-MI vessels. Segments that will be analyzed include: left main, proximal, mid and distal left anterior descending, first and second diagonal branch, proximal and distal left circumflex, first or largest space obtuse marginal, proximal, mid and distal right coronary artery. Subjects will have an ejection fraction of greater than 30% determined by catheterization or radionuclide ventriculography or ECHO cardiogram at the time of the qualifying angiogram or within the previous three months of the acceptance of the qualifying angiogram provided no intervening event such as a thrombotic event or procedure such as PTCA has occurred.

Generally, due to the number of patients and the physical limitations of any one facility, the study is carried out at multiple sites. At entry into the study, subjects undergo quantitative coronary angiography as well as B-mode carotid artery ultrasonography and assessment of carotid arterial compliance at designated testing centers. This establishes baselines for each subject. Once admitted into the test, subjects are randomized to receive amlodipine besylate (10 mgs) and placebo or atorvastatin calcium (80 mgs) and placebo or amlodipine besylate (10 mgs) and atorvastatin calcium (80 mgs). All doses set forth in this protocol are per day doses. The amount of amlodipine besylate may be varied as required. Generally, a subject will start out taking 10 mg and the amount will be titrated down to as little as 5 mg as determined by the clinical physician. The amount of atorvastatin calcium will similarly be titrated down from 80 mg if it is determined by the physician to be in the best interests of the subject. It will be recognized by a skilled person that the free base form or other salt forms of amlodipine besylate or the free base form or other salt forms of atorvastatin calcium may be used in this invention. Calculation of the dosage amount for these other forms of atorvastatin calcium and amlodipine besylate is easily accomplished by performing a simple ratio relative to the molecular weights of the species involved.

The subjects are monitored for a one to three year period, generally three years being preferred. B-mode carotid ultrasound assessment of carotid artery atherosclerosis and compliance are performed at regular intervals throughout the study.

Generally, six month intervals are suitable. Typically this assessment is performed using B-mode ultrasound equipment. However, a person skilled in the art may use other methods of performing this assessment. Coronary angiography is performed at the conclusion of the one to three year treatment period. The baseline and post-treatment angiograms and the intervening carotid artery B-mode ultrasonograms are evaluated for new lesions or progression of existing atherosclerotic lesions. Arterial compliance measurements are assessed for changes from baseline and over the 6 month evaluation periods.

The primary objective of this study is to show that the combination of amlodipine or pharmaceutically acceptable acid addition salts thereof and atorvastatin or pharmaceutically acceptable salts thereof reduces the progression of atherosclerotic lesions as measured by quantitative coronary angiography (QCA) in subjects with clinical coronary artery disease. QCA measures the opening in the lumen of the arteries measured.

The primary endpoint of the study is the change in the average mean segment diameter of the coronary artery tree.

Thus, the diameter of an arterial segment is measured at various portions along the length of that segment. The average diameter of that segment is then determined. After the average segment diameter of many segments has been determined, the average of all segment averages is determined to arrive at the average mean segment diameter. The mean segment diameter of subjects taking atorvastatin or pharmaceutically acceptable salts thereof and amlodipine or pharmaceutically acceptable acid addition salts thereof will decline more slowly, will be halted completely, or there will be an increase in the mean segment diameter. These results represent slowed progression of atherosclerosis, halted progression of atherosclerosis and regression of atherosclerosis, respectively.

The secondary objective of this study is to show that the combination of amlodipine or a pharmaceutically acceptable acid addition salt thereof and atorvastatin or a pharmaceutically salt thereof reduces the rate of progression of atherosclerosis in the carotid arteries as measured by the slope of the maximum intimal-medial thickness measurements averaged over 12 separate wall segments (Mean Max) as a function of time, more than does amlodipine or a pharmaceutically acceptable acid addition salt thereof or atorvastatin or a pharmaceutically acceptable salt thereof alone. The intimal-medial thickness of subjects taking atorvastatin or a pharmaceutically acceptable salt thereof and amlodipine or a pharmaceutically acceptable acid addition salt thereof will increase more slowly, will cease to increase or will decrease. These results represent slowed progression of atherosclerosis, halted progression of atherosclerosis and regression of atherosclerosis, respectively.

The utility of the compounds of the present invention as medical agents in the treatment of angina pectoris in mammals (e.g., humans) is demonstrated by the activity of the compounds of this invention in conventional assays and the clinical protocol described below:

Effect of Amlodipine and Atorvastatin, Alone and in Combination, on the Treatment of Angina This study is a double blind, parallel arm, randomized study to show the effectiveness of amlodipine or pharmaceutically acceptable acid addition salts thereof and atorvastatin or pharmaceutically acceptable salts thereof given in combination in the treatment of symptomatic angina.

Entry criteria: Subjects are males or females between 18 and 80 years of age with a history of typical chest pain associated with one of the following objective evidences of cardiac ischemia: (1) stress test segment elevation of about one millimeter or more from the ECG; (2) positive treadmill stress test; (3) new wall motion abnormality on ultrasound; or (4) coronary angiogram with a significant qualifying stenosis. Generally a stenosis of about 30–50% is considered to be significant.

Each subject is evaluated for about ten to thirty-two weeks. At least ten weeks are generally required to complete the study. Sufficient subjects are used in this screen to ensure that about 200 to 800 subjects and preferably about 400 subject are evaluated to complete the study. Subjects are screened for compliance with the entry criteria, set forth below, during a four week run in phase. After the screening criteria are met, subjects are washed out from their current anti-anginal medication and stabilized on a long acting nitrate such as, for example, nitroglycerin, isosorbide-5-mononitrate or isosorbide dinitrate. The term "washed out", when used in connection with this screen, means the withdrawal of current anti-anginal medication so that substantially all of said medication is eliminated from the body of the subject. A period of eight weeks is preferably allowed for both the wash out period and for the establishment of the subject on stable doses of said nitrate. Subjects having one or two attacks of angina per week while on stable doses of long acting nitrate are generally permitted to skip the wash out phase. After subjects are stabilized on nitrates, the subjects enter the randomization phase provided the subjects continue to have either one or two angina attacks per week. In the randomization phase, the subjects are randomly placed into one of the four arms of the study set forth below. After completing the wash out phase, subjects in compliance with the entry criteria undergo twenty four hour ambulatory electrocardiogram (ECG) such as Holter monitoring, exercise stress testing such as a treadmill and evaluation of myocardial perfusion using PET (photon emission tomography) scanning to establish a baseline for each subject. When conducting a stress test, the speed of the treadmill and the gradient of the treadmill can be controlled by a technician. The speed of the treadmill and the angle of the gradient are generally increased during the test. The time intervals between each speed and gradient increase is generally determined using a modified Bruce Protocol.

After the baseline investigations have been completed, subjects are initiated on one of the following four arms of the study: (1) placebo; (2) atorvastatin calcium (about 2.5 mg to about 160 mg); (3) amlodipine besylate(about 2.5 mg to about 20 mg); or (4) a combination of the above doses of amlodipine besylate and atorvastatin calcium together. The subjects are then monitored for two to twenty four weeks. It will be recognized by a skilled person that the free base form or other salt forms of amlodipine besylate or the free base form or other salt forms of atorvastatin calcium may be used in this invention. Calculation of the dosage amount for these other forms of atorvastatin calcium and amlodipine besylate is easily accomplished by performing a simple ratio relative to the molecular weights of the species involved.

After the monitoring period has ended, subjects will undergo the following investigations: (1) twenty four hour ambulatory ECG, such as Holter monitoring; (2) exercise stress testing (e.g. treadmill using said modified Bruce Protocol); and (3) evaluation of myocardial perfusion using PET scanning. Patients keep a diary of painful ischemic events and nitroglycerine consumption. It is generally desirable to have an accurate record of the number of anginal attacks suffered by the patient during the duration of the test. Since a patient generally takes nitroglycerin to ease the pain of an anginal attack, the number of times that the patient administers nitroglycerine provides a reasonably accurate record of the number of anginal attacks.

To demonstrate the effectiveness of the drug combination of this invention, and to determine the dosage amounts of the drug combination of this invention, the person conducting the test will evaluate the subject using the tests described. Successful treatment will yield fewer instances of ischemic events as detected by ECG, will allow the subject to exercise longer or at a higher intensity level on the treadmill, or to exercise without pain on the treadmill, or will yield better perfusion or fewer perfusion defects on photoemission tomography (PET).

The utility of the compounds of the present invention as medical agents in the treatment of hypertension and hyperlipidemia in mammals (e.g., humans) suffering from a combination of hypertension and hyperlipidemia is demonstrated by the activity of the compounds of this invention in conventional assays and the clinical protocol described below:

Effect of Amlodipine and Atorvastatin, Alone and in Combination, on the Treatment of Subjects Having Both Hypertension and Hyperlipidemia This study is a double blind, parallel arm, randomized study to show the effectiveness of amlodipine or pharmaceutically acceptable acid addition salts thereof and atorvastatin or pharmaceutically acceptable salts thereof given in combination in controlling both hypertension and hyperlipidemia in subjects who have mild, moderate, or severe hypertension and hyperlipidemia.

Each subject is evaluated for 10 to 20 weeks and preferably for 14 weeks. Sufficient subjects are used in this screen to ensure that about 400 to 800 subjects are evaluated to complete the study.

Entry criteria: Subjects are male or female adults between 18 and 80 years of age having both hyperlipidemia and hypertension. The presence of hyperlipidemia is evidenced by evaluation of the low density lipoprotein (LDL) level of the subject relative to certain positive risk factors. If the subject has no coronary heart disease (CHD) and has less than two positive risk factors, then the subject is considered to have hyperlipidemia if the LDL of the subject is greater than or equal to 190. If the subject has no CHD and has two or more positive risk factors, then the subject is considered to have hyperlipidemia if the LDL of the subject is greater than or equal to 160. If the subject has CHD, then the subject is considered to have hyperlipidemia if the LDL of the subject is greater than or equal to 130.

Positive risk factors include (1) male over 45, (2) female over 55 wherein said female is not undergoing hormone replacement therapy (HRT), (3) family history of premature cardiovascular disease, (4) the subject is a current smoker, (5) the subject has diabetes, (6) an HDL of less than 45, and (7) the subject has hypertension. An HDL of greater than 60 is considered a negative risk factor and will offset one of the above mentioned positive risk factors.

The presence of hypertension is evidenced by a sitting diastolic blood pressure (BP) of greater than 90 or sitting systolic BP of greater than 140. All blood pressures are generally determined as the average of three measurements taken five minutes apart.

Subjects are screened for compliance with the entry criteria set forth above. After all screening criteria are met, subjects are washed out from their current antihypertensive and lipid lowering medication and are placed on the NCEP ATP II Step 1 diet. The NCEP ATP II (adult treatment panel, 2nd revision) Step 1 diet sets forth the amount of saturated and unsaturated fat which can be consumed as a proportion of the total caloric intake. The term "washed out" where used in connection with this screen, means the withdrawal of current antihypertensive and lipid lowering medication so that substantially all of said medication is eliminated from the body of the subject. Newly diagnosed subjects generally remain untreated until the test begins. These subjects are also placed on the NCEP Step 1 diet. After the four week wash out and diet stabilization period, subjects undergo the following baseline investigations: (1) blood pressure and (2) fasting lipid screen. The fasting lipid screen determines baseline lipid levels in the fasting state of a subject. Generally, the subject abstains from food for twelve hours, at which time lipid levels are measured.

After the baseline investigations are performed subjects are started on one of the following: (1) a fixed dose of amlodipine besylate, generally about 2.5 to 10 mg; (2) a fixed dose of atorvastatin calcium, generally about 10 to 80 mg; or (3) a combination of the above doses of amlodipine besylate and atorvastatin calcium together. Subjects remain on these doses for a minimum of six weeks, and generally for no more than eight weeks. It will be recognized by a skilled person that the free base form or other salt forms of amlodipine besylate or the free base form or other salt forms of atorvastatin calcium may be used in this invention. Calculation of the dosage amount for these other forms of atorvastatin calcium and amlodipine besylate is easily accomplished by performing a simple ratio relative to the molecular weights of the species involved. The subjects return to the testing center at the conclusion of the six to eight weeks so that the baseline evaluations can be repeated. The blood pressure of the subject at the conclusion of the study is compared with the blood pressure of the subject upon entry. The lipid screen measures the total cholesterol, LDL-cholesterol, HDL-cholesterol, triglycerides, apoB, VLDL (very low density lipoprotein) and other components of the lipid profile of the subject. Improvements in the values obtained after treatment relative to pretreatment values indicate the utility of the drug combination.

The utility of the compounds of the present invention as medical agents in the management of cardiac risk in mammals (e.g., humans) at risk for an adverse cardiac event is demonstrated by the activity of the compounds of this invention in conventional assays and the clinical protocol described below:

Effects of Amlodipine and Atorvastatin, Alone and in Combination on Subjects at Risk of Future Cardiovascular Events This study is a double blind, parallel arm, randomized study to show the effectiveness of amlodipine or pharmaceutically acceptable acid addition salts thereof and atorvastatin or pharmaceutically acceptable salts thereof given in combination are effective in reducing the overall calculated risk of future events in subjects who are at risk for having future cardiovascular events. This risk is calculated by using the Framingham Risk Equation. A subject is considered to be at risk of having a future cardiovascular event if that subject is more than one standard deviation above the mean as calculated by the Framingham Risk Equation. The study is used to evaluate the efficacy of a fixed combination of amlodipine and atorvastatin in controlling cardiovascular risk by controlling both hypertension and hyperlipidemia in patients who have both mild to moderate hypertension and hyperlipidemia.

Each subject is evaluated for 10 to 20 weeks and preferably for 14 weeks. Sufficient subjects are recruited to ensure that about 400 to 800 subjects are evaluated to complete the study.

Entry criteria: Subjects included in the study are male or female adult subjects between 18 and 80 years of age with a baseline five year risk which risk is above the median for said subject's age and sex, as defined by the Framingham Heart Study, which is an ongoing prospective study of adult men and women showing that certain risk factors can be used to predict the development of coronary heart disease. The age, sex, systolic and diastolic blood pressure, smoking habit, presence or absence of carbohydrate intolerance, presence or absence of left ventricular hypertrophy, serum cholesterol and high density lipoprotein (HDL) of more than one standard deviation above the norm for the Framingham Population are all evaluated in determining whether a patient is at risk for adverse cardiac event. The values for the risk factors are inserted into the Framingham Risk equation and calculated to determine whether a subject is at risk for a future cardiovascular event.

Subjects are screened for compliance with the entry criteria set forth above. After all screening criteria are met, patients are washed out from their current antihypertensive and lipid lowering medication and any other medication which will impact the results of the screen. The patients are then placed on the NCEP ATP II Step 1 diet, as described above. Newly diagnosed subjects generally remain untreated until the test begins. These subjects are also placed on the NCEP ATP II Step 1 diet. After the four week wash out and diet stabilization period, subjects undergo the following baseline investigations: (1) blood pressure; (2) fasting; (3) lipid screen; (4) glucose tolerance test; (5) ECG; and (6) cardiac ultrasound. These tests are carried out using standard procedures well known to persons skilled in the art. The ECG and the cardiac ultrasound are generally used to measure the presence or absence of left ventricular hypertrophy.

After the baseline investigations are performed patients will be started on one of the following: (1) a fixed dose of amlodipine (about 2.5 to 10 mg); (2) a fixed dose of atorvastatin (about 10 to 80 mg); or (3) the combination of the above doses of amlodipine and atorvastatin. It will be recognized by a skilled person that the free base form or other salt forms of amlodipine besylate or the free base form or other salt forms of atorvastatin calcium may be used in this invention. Calculation of the dosage amount for these other forms of atorvastatin calcium and amlodipine besylate is easily accomplished by performing a simple ratio relative to the molecular weights of the species involved. Patients are kept on these doses and are asked to return in six to eight weeks so that the baseline evaluations can be repeated. At this time the new values are entered into the Framingham Risk equation to determine whether the subject has a lower, greater or no change in the risk of future cardiovascular event.

The above assays demonstrating the effectiveness of amodipine or pharmaceutically acceptable acid addition salts thereof and atorvastatin or pharmaceutically acceptable salts thereof in the treatment of angina pectoris, atherosclerosis, hypertension and hyperlipidemia together, and the management of cardiac risk, also provide a means whereby the activities of the compounds of this invention can be compared between themselves and with the activities of other known compounds. The results of these comparisons are useful for determining dosage levels in mammals, including humans, for the treatment of such diseases.

The following dosage amounts and other dosage amounts set forth elsewhere in the specification and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject and the presence of diseases, e.g., diabetes, in the subject. All doses set forth herein, and in the appendant claims, are daily doses.

In general, in accordance with this invention, amlodipine besylate is generally administered in a dosage of about 2.5 mg to about 20 mg. Preferably, amlodipine besylate is administered in a dosage of about 5 mg to about 10 mg. It will be recognized by a skilled person that the free base form or other salt forms of amlodipine besylate may be used in this invention. Calculation of the dosage amount for these other forms of or the free base form or other salt forms of amlodipine besylate is easily accomplished by performing a simple ratio relative to the molecular weights of the species involved.

In general, in accordance with this invention, atorvastatin is administered in a dosage of about 2.5 mg to about 160 mg. Preferably, atorvastatin is administered in a dosage of about 10 mg to about 80 mg. It will be recognized by a skilled person that the free base form or other salt forms of atorvastatin calcium may be used in this invention. Calculation of the dosage amount for these other forms of or the free base form or other salt forms of atorvastatin calcium is easily accomplished by performing a simple ratio relative to the molecular weights of the species involved.

The compounds of the present invention are generally administered in the form of a pharmaceutical composition comprising at least one of the compounds of this invention together with a pharmaceutically acceptable carrier or diluent. Thus, the compounds of this invention can be administered either individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

The combination of this invention may also be administered in a controlled release formulation such as a slow release or a fast release formulation. Such controlled release dosage formulations of the combination of this invention may be prepared using methods well known to those skilled in the art. The method of preferred administration will be determined by the attendant physician or other person skilled in the art after an evaluation of the subject's condition and requirements. The generally preferred formulation of amlodipine is Norvasc®. The generally preferred formulation of atorvastatin is Lipitor®.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Methods of preparing various pharmaceutical compositions with a certain amount of active ingredient are known, or will be apparent in light of this disclosure, to those skilled in this art. For examples, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the condition or disease of the subject being treated.

Since the present invention relates to the treatment of diseases and conditions with a combination of active ingredients which may be administered separately, the invention also relates to combining separate pharmaceutical compositions in kit form. The kit includes two separate pharmaceutical compositions: amlodipine or a pharmaceutically acceptable acid addition salt thereof and atorvastatin or a pharmaceutically acceptable salt thereof. The kit includes container means for containing the separate compositions such as a divided bottle or a divided foil packet, however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It should be understood that the invention is not limited to the particular embodiments described herein, but that various changes and modifications may be made without departing from the spirit and scope of this novel concept as defined by the following claims.

What is claimed is:

1. A method for treating a mammal suffering from combined hypertension and hyperlipidemia comprising administering to said mammal
   (a) an amount of a first compound, said first compound being amlodipine or a pharmaceutically acceptable acid addition salt thereof; and
   (b) an amount of a second compound, said second compound being atorvastatin or a pharmaceutically acceptable salt thereof;
wherein said first compound and said second compound are administered together in a single pharmaceutical composition with a pharmaceutically acceptable carrier or diluent.

2. The method of claim 1 comprising amlodipine besylate.

3. The method of claim 2 comprising the hemicalcium salt of atorvastatin.

4. The method of claim 1 comprising the hemicalcium salt of atorvastatin.

5. A method of treating a mammal which has been diagnosed as suffering from hypertension and hyperlipidemia or the risk of hypertension and hyperlipidemia which would benefit from therapy by the combined administration of the active ingredients designated as (a) and (b) below, and therefore administration of both (a) and (b) has been prescribed, which comprises administering to said mammal so diagnosed and prescribed
   (1) an amount of a first active ingredient (a), said first active ingredient (a) being amlodipine or a pharmaceutically acceptable acid addition salt thereof; and
   (2) an amount of a second active ingredient (b), said second active ingredient (b) being atorvastatin or a pharmaceutically acceptable salt thereof;
wherein said first active ingredient (a) and said second active ingredient (b) are administered together in a single pharmaceutical composition with a pharmaceutically acceptable carrier or diluent.

6. The method of claim 5 wherein active ingredient (a) is amlodipine besylate.

7. The method of claim 6 wherein active ingredient (b) is the hemicalcium salt of atorvastatin.

8. The method of claim 5 wherein active ingredient (b) is the hemicalcium salt of atorvastatin.

9. A method of treating combined hypertension and hyperlipidemia in a mammal which has been examined for both hypertension and hyperlipidemia by a medical practitioner and diagnosed as in need of therapy for said hypertension and hyperlipidemia by the joint administration of the active ingredients designated as (a) and (b) below, which comprises administering to said mammal
   (1) an amount of a first active ingredient (a), said first active ingredient (a) being amlodipine or a pharmaceutically acceptable acid addition salt thereof; and
   (2) an amount of a second active ingredient (b), said second active ingredient (b) being atorvastatin or a pharmaceutically acceptable salt thereof;
wherein said first active ingredient (a) and said second active ingredient (b) are administered together in single pharmaceutical composition with a pharmaceutically acceptable carrier or diluent.

10. The method of claim 9 wherein active ingredient (a) is amlodipine besylate.

11. The method of claim 10 wherein active ingredient (b) is the hemicalcium salt of atorvastatin.

12. The method of claim 9 wherein active ingredient (b) is the hemicalcium salt of atorvastatin.

* * * * * gi

(12) EX PARTE REEXAMINATION CERTIFICATE (8749th)
United States Patent
Buch

(10) Number: US 6,455,574 C1
(45) Certificate Issued: Dec. 13, 2011

(54) THERAPEUTIC COMBINATION

(75) Inventor: Jan Buch, Greenwich, CT (US)

(73) Assignee: Pfizer Products Inc., Groton, CT (US)

Reexamination Request:
No. 90/011,053, Jun. 17, 2010

Reexamination Certificate for:
Patent No.: 6,455,574
Issued: Sep. 24, 2002
Appl. No.: 09/512,914
Filed: Feb. 25, 2000

Related U.S. Application Data

(63) Continuation of application No. PCT/IB98/01225, filed on Aug. 11, 1998.
(60) Provisional application No. 60/057,275, filed on Aug. 29, 1997.

(51) Int. Cl.
*A61K 31/40* (2006.01)
*A61K 31/435* (2006.01)
*A61K 31/44* (2006.01)

(52) U.S. Cl. .......................... 514/427; 514/277; 514/356; 514/408; 514/422; 514/423

(58) Field of Classification Search .................. 514/427
See application file for complete search history.

(56) References Cited

To view the complete listing of prior art documents cited during the proceeding for Reexamination Control Number 90/011,053, please refer to the USPTO's public Patent Application Information Retrieval (PAIR) system under the Display References tab.

*Primary Examiner* — Dwayne Jones

(57) ABSTRACT

This invention relates to pharmaceutical combinations of amlodipine or a pharmaceutically acceptable acid addition salt thereof and atorvastatin or a pharmaceutically acceptable salt thereof, kits containing such combinations and methods of using such combinations to treat subjects suffering from angina pectoris, atherosclerosis, combined hypertension and hyperlipidemia and to treat subjects presenting with symptoms of cardiac risk, including humans. This invention also relates to additive and synergistic combinations of amlodipine and atorvastatin whereby those synergistic combinations are useful in treating subjects suffering from angina pectoris, atherosclerosis, combined hypertension and hyperlipidemia and those subjects presenting with symptoms of cardiac risk, including humans.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

* * * * *